(12) United States Patent
Zoebisch (10) Patent No.: US 7,797,144 B2
(45) Date of Patent: Sep. 14, 2010

(54) MOLECULAR MODELING METHOD AND SYSTEM

(76) Inventor: Eve Zoebisch, 1455 Topar Ave., Los Altos, CA (US) 94024-5943

( * ) Notice: Subject to any disclaimer, the term of this patent is extended or adjusted under 35 U.S.C. 154(b) by 1195 days.

(21) Appl. No.: 11/084,307

(22) Filed: Mar. 18, 2005

(65) Prior Publication Data

US 2006/0212282 A1   Sep. 21, 2006

(51) Int. Cl.
*G06G 7/58* (2006.01)
*G01N 33/48* (2006.01)

(52) U.S. Cl. .............................. 703/11; 702/19; 702/20
(58) Field of Classification Search ....................... None
See application file for complete search history.

(56) References Cited

U.S. PATENT DOCUMENTS

| | | | |
|---|---|---|---|
| 4,855,931 A | 8/1989 | Saunders |
| 5,307,287 A | 4/1994 | Cramer et al. |
| 5,424,963 A | 6/1995 | Turner et al. |
| 5,612,894 A | 3/1997 | Wertz |
| 5,915,230 A | 6/1999 | Berne et al. |
| 6,460,014 B1 | 10/2002 | Waldman et al. |
| 6,785,665 B2 | 8/2004 | Sun |
| 2003/0216867 A1 | 11/2003 | Campbell et al. |
| 2003/0216900 A1 | 11/2003 | Rosenthal |

FOREIGN PATENT DOCUMENTS

WO      WO 97/46949 A1     12/1997

OTHER PUBLICATIONS

Lorrain, et al., Electromagnetic Fields and Waves, 1970, pp. 40-90, Second Edition, W.H. Freeman and Company, San Francisco.
Cheatham, et al., "Molecular Dynamics Simulation of Nucleic Acids . . . ," Biopolymers, 2001, pp. 232-256, vol. 56, John Wiley & Sons, Inc., NY.
Ponder, et al., "Force Fields for Protein Simulations," Advances in Protein Chemistry, 2003, pp. 27-85, vol. 66, Elsevier Inc., NY.
Neves-Petersen, M.T., et al., "Protein Electrostatics: A Review of the . . . " Biotech Ann Rev, 2003, pp. 315-395, vol. 9, Elsevier, New York, New York.
Simonson, T., et al., "Charge Screening and the Dielectric Constant . . . " Jour. Amer. Chem. Society, 1996, pp. 8452-8458, vol. 118, No. 35, ACS, Wash., DC.
Goel, N. S., et al., "Electrostatic Field in Inhomogeneous Dielectric . . . " Jour. Comp. Physics, 1995, pp. 180-188, vol. 118, No. 4, Academic Press, London.
Cramer, C. J., et al., "Continuum.Solvation Methods: Classical and . . . " Reviews in Comp. Chem., 1995, pp. 1-72, vol. VI, VCH Pub., New York, NY.
Karshikoff, A., et al., "Electrostatic Properties of Two Porin Channels" Jour. Mol. Biology,1994, pp. 372-384, vol. 240, No. 4, Academic Press, London.
Brooks, B. R., et al., "CHARMM: A Program for Macromolecular Energy . . . " Jour. of Comp. Chem.,1983, pp. 187-217; vol. 9, No. 2, Wiley&Sons, Chichester, GB.
Warshel, A., et al., "Theoretical Studies of Enzymic Reactions: Dielectric . . . " Jour. Mol. Biology, 1976, pp. 227-249, vol. 103, Academic Press, London.

*Primary Examiner*—Shubo (Joe) Zhou
(74) *Attorney, Agent, or Firm*—Kevin Roe (57) ABSTRACT

A molecular modeling method and system to provide a dielectric function that reflects the plurality of models simultaneously used in molecular modeling. For interactions similar to those used during the development of a charge model, the dielectric is similar to the charge model dielectric. In a second embodiment, an approximation for electrostatic/electrodynamics modeling is provided that analyzes charge distribution and determines groups of charges that can be treated as a whole at moderate distances.

16 Claims, 11 Drawing Sheets

(PRIOR ART)

MOLECULAR MODELING METHOD AND SYSTEM

BACKGROUND OF THE INVENTION

1. Field of the Invention

This invention relates generally to providing a method and system to facilitate molecular modeling, and more specifically to providing a method and system to approximate the electrostatics and electrodynamics functions used in molecular modeling software.

2. Description of the Prior Art

Significant advances have been made in predicting, studying, and quantifying the nature of interatomic and intermolecular interactions with the use of computer models. Although such computer models can be useful in testing and validating a theory concerning the nature of these interactions, computer models find especially useful application in reducing the time required to develop new materials with desirable properties. Materials that may be developed with additional efficiency through the use of computer models include polymers, pesticides, herbicides, pharmaceuticals, semiconductor materials for integrated circuits, and petrochemicals.

Several modeling techniques are used to study chemical systems. These techniques are referred to as simulations, models, methods, approximations, and so forth. Here all techniques are referred to as models. Typically, the model selected provides a user of the model with a particular compromise between physical accuracy and the computing resources required to run the model. Quantum mechanical calculations can be performed with a high degree of accuracy, but are very expensive in terms of the computer time required to perform them. In those fields described above, where new polymers, drugs, and other products are being developed, it is more useful to use modeling techniques that requires less investment in computing resources, so that more candidate materials or molecules can be analyzed in a shorter time period for the properties desired.

Force Fields

A general class of models called force fields is frequently used. A force field uses analytical classical equations to describe molecules, e.g., the potential energy of a diatomic molecule can be modeled with a harmonic equation. Occasionally non-analytic terms are included, e.g., induced polarization terms. These functions are significantly simpler computationally than performing the more correct and mathematically complex quantum mechanical calculations.

Force fields are developed to reproduce experimental data or calculation results, generally quantum mechanics calculations. The selection of appropriate parameters and force field functional dependencies is a significant factor in the success of the model. Furthermore, the number of fitted parameters used in the model relative to the number of measurable or calculable values relevant to the system being modeled should be as low as possible to minimize the possibility of chance correlations.

New force field functions are continually under development to increase agreement with experiment and quantum results, to maximize the number of observables relative to the number of parameters, and to limit the necessity of performing computationally expensive calculations.

The potential energy function is the energy of a set of atoms as a function of atomic coordinates. One class of potential energy functions is the force field function. For any chosen force field function and a given set of atoms, the location of the atoms, the types of atoms, and the bonds between the atoms define a potential energy field. For a given set of atomic coordinates (configuration) the energy is well defined. On rare occasions there is bond breaking and bond making, generally explicitly defined by the user. The potential energy field is usually expressed as a sum of terms, with each term representing a particular class of interaction.

Most force fields include terms that represent bonded interactions such as bond stretching and contraction, angle stretching and contraction, rotation about a dihedral bond, out-of-plane deformation, cross terms of the above and any other term or parameter that the method developer considers to be significant. These interactions are sometimes referred to as intramolecular interactions.

Non-bonded, or intermolecular interaction potential energy generally includes a van der Waals interaction and a model using electrostatic interactions. The van der Waals (vdW) term may take a variety of forms. In general, vdW terms are mildly attractive at large separations and become very repulsive at small atomic separations. Different known parameterizations of the van der Waals term, and intramolecular force parameters, may be used.

A general expression for a potential energy field generally used for molecular modeling may thus be described as follows:

$$V_E = \text{intramolecular terms} + \text{van der Waals} + \text{electrostatic terms} \quad (1)$$

The energy, $V_E$, is the value of the potential energy field for a particular configuration of atoms. Forces acting on the atoms are determined by calculating the gradient of the potential energy field at the atomic coordinates determined by the configuration.

Charge Model

The electrostatic term is calculated using charges from a charge model. The charge model is generally developed for a set of atoms such as a molecule (composed of electrons and nuclei), an amino acid, a nucleic acid, a cell in a regular array, an aggregate, or other group of atoms (henceforth any said set of atoms is called a substructure).

The probability of electron position is provided by the quantum mechanics wavefunction, which is the solution to the Shroedinger Equation. This probability is generally considered to describe a charge distribution. Chemists frequently approximate this charge distribution with a classical description composed of point charges, dipoles, quadrupoles, and higher multipoles. The choice of charges and the methodology used to determine the charges is called a charge model.

Different techniques have been used to develop charge models. For example, the method pioneered by Kollmann et al. is disclosed in "Force Fields for Protein Simulations," by J. W. Ponder and D. A. Case in *Adv. Prot. Chem.*, vol. 66, pp. 27-85 (2003); and in "Molecular Dynamics Simulation of Nucleic Acids: Successes, Limitations, and Promise," by T. E. Cheatham, III and M. A. Young in *Biopolymers*, vol. 56, pp. 232-256 (2001); which are hereby incorporated by reference. This method uses point charges placed at atom centers to reproduce the electrostatic field around the molecule as calculated by placing test charges in the molecule's periphery in a quantum mechanics calculation. In other methods the charge model reproduces other properties, such as hydrogen bond strength. In addition there are programs that assign charges based on the bonding structure of the molecule. For the purposes of this patent an atomistic charge model is a charge model that is any combination of the following: (1) assigns fractional electron charges to the vast majority of atoms in a chemical system, (2) assigns dipoles to the vast majority of the atoms in a chemical system, (3) assigns charges between the vast majority of atoms that are bonded, and (4) assigns dipoles between the vast majority of atoms that are bonded. Molecular modeling frequently uses this charge model to calculate the electrostatic potential between molecules and between different parts of the same molecule.

Dielectric Model

Molecular modeling simultaneously uses multiple independent models where the dielectric terms do not necessarily correspond with each other. The dielectric of a material is a macroscopic property. Poisson's equation describing electrostatics was developed to describe electrostatic interactions on a macroscopic scale, and the dielectric concept was incorporated into the equations to accommodate the dielectric properties of matter. However, there is no term for a dielectric in the Schroedinger Equation, which applies to a molecular scale. In the work of Kollman et al. noted above, the dielectric was not included in the classical equations. This has the effect of setting the classical dielectric to one, i.e., D=1. Alternately, a dielectric of 2 or 4 is frequently used for protein calculations.

There are various approaches to handle a dielectric when using classical electrostatic (macroscopic) equations to model molecules. The dielectric properties of the molecule are implicitly or explicitly incorporated into the model. When developing a charge model, the chosen dielectric is incorporated into the choice of partial charge, i.e., a charge is chosen which produces the desired properties given the dielectric used. In the charge model of Kollman et al., the charges create an electrostatic field about the molecule that approximates the quantum result given a dielectric of one. When there are two molecules, Coulomb's equation describes the interaction energy between them.

Figure 1:
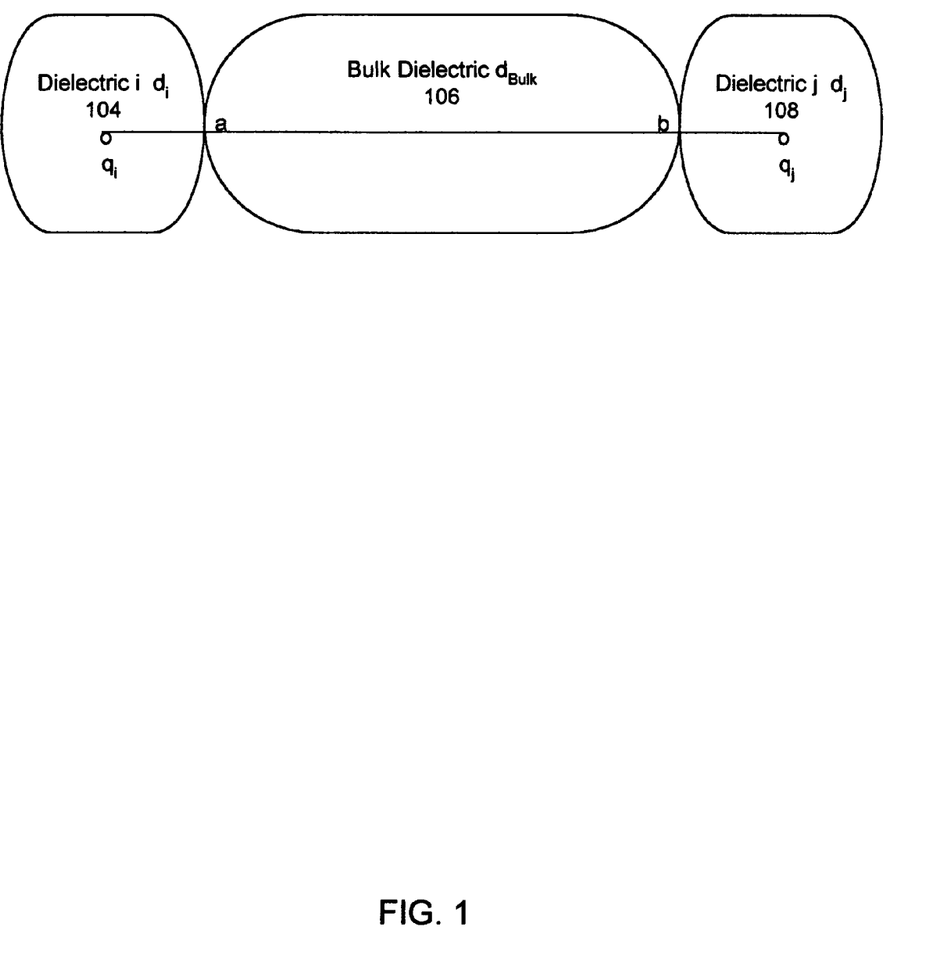
FIG. 1 illustrates two charges in respective dielectrics separated by a bulk dielectric.

As an example of the prior art approach, consider the electrostatic potential between two charges $q_i$ and $q_j$, at points i and j respectively, shown in FIG. 1 where $q_i$ is embedded in dielectric $d_i$ 104, $q_j$ is embedded in dielectric $d_j$, 108, and there is dielectric $d_{bulk}$ 106 in between $d_i$ and $d_j$. The electrostatic potential between $q_i$ and $q_j$ can be calculated in several steps. The electric field intensity, E, at point j due to $q_i$ is determined by calculating the electric field at point a given dielectric $d_i$, 104, calculating the change in E in traversing the dielectric $d_{bulk}$ 106 in going from point a to point b, and then calculating E in traversing the dielectric $d_j$ 108 from point b to point j. Electrostatic potential can then be calculated from E and the value of the charge $q_j$.

Composite Charge Model

In the prior art, algorithms for calculation of intermolecular electrostatic potential were modeled by detailed calculation of charge-charge interactions.

$$E=\Sigma_{i>j}(q_iq_j)/(Dr_{ij}) \qquad (2)$$

In some situations a group of charges can be handled together. When the distance between the test point and the set of charges is sufficiently large, then the electrostatic field created by a set of charges is approximated with a function of the total charge, the total dipole, total quadrupole, and higher total charge multipoles. For example, the textbook *"Electromagnetic Fields and Waves,"* by Paul Lorrain and Dale Corson, 1970, (pp. 62, 65, and 70), which is hereby incorporated by reference, explains how to approximate an electrostatic potential. An excerpt of the approximation method follows.

"The potential due to an arbitrary charge distribution at a point outside the distribution such that $r>r^1$ is the same as: (a) the potential of a point charge equal to the net charge of the distribution, plus (b) that of a point dipole with a dipole moment equal to the dipole moment of the distribution, plus (c) that of a point quadrupole with a quadrupole moment equal to that of the distribution, and so on, all located at the origin. where $r^1$ is the maximal distance between the origin and a charge (distribution). The potential due to a dipole moment varies as $1/r^2$ and the potential due to a quadrupole moment varies as $1/r^3$." The impact of this result is evident in the charges found in charge models.

The point charge model has produced individual atom-atom interactions that are large. For example, consider the potential calculated using the Amber 1998 [reference] parameter set. The potential between the two aliphatic terminal carbons in two amino acid Leucine molecules that are 45 Angstroms (A) apart is 10 kcal/mole. (i.e., $Q_iQ_j/r_{ij}$=300(0.3)(0.3)/45=10 kcal), which is large. From an experimental perspective, the electrostatic potential between the side chains in Leucine molecules that are 45A apart is negligible. The apparent contradiction is resolved by the composite charge result noted above; in a calculation the large 10 kcal/mole term is counterbalanced by the similar terms of opposite sign in neighboring atoms and the result is small.

The large number of charges generated by the charge model introduces further problems. There may be very large number of electrostatic interactions. For example, in a protein with 3000 atoms, there are $\sim n^2/2$ interactions or $\sim 4,500,000$ terms. In many applications, the electrostatic potential is sampled repeatedly and the computer time required becomes quite large. Significant effort has been expended to decrease the computer time. Three techniques are noted below.

Cutoff distances have been explored where all interactions from charges greater than an "R" distance apart are set to zero. "R" is called the cutoff distance. This produces a discontinuous function at the cutoff distance, and various means have been developed to smooth this function. While smoothing makes the function differentially continuous, the cutoff approach introduces large error into the calculations.

In U.S. Pat. No. 5,612,894, which is hereby incorporated by reference, Wertz discloses an alternative procedure to reduce the number of electrostatic calculations. This procedure determines the sensitivity (importance) of a desired quantity to a given interaction and restricts the calculation of interactions with low sensitivity. This method requires techniques to recalculate whether a given interaction is important and techniques to "remember" the important ones. The interactions are separated into classes of varying importance. In some cases terms that could be in the same category to provide the counterbalancing charge terms noted above will be in different classes.

In U.S. Pat. No. 5,915,230, which is hereby incorporated by reference, Berne et al. disclose an approximation for electrostatic potential at a distance from a set of charges. A three-dimensional space is divided into cubic volumes (boxes) and the charges inside a box are handled as a set. Unfortunately the division into boxes is artificial and counterbalancing charges can be in different boxes. Charge models depend on the canceling effects at large distances as noted above. Separating the opposite, canceling charges into different boxes creates computational artifacts in the functions and makes them less stable.

Figure 2:
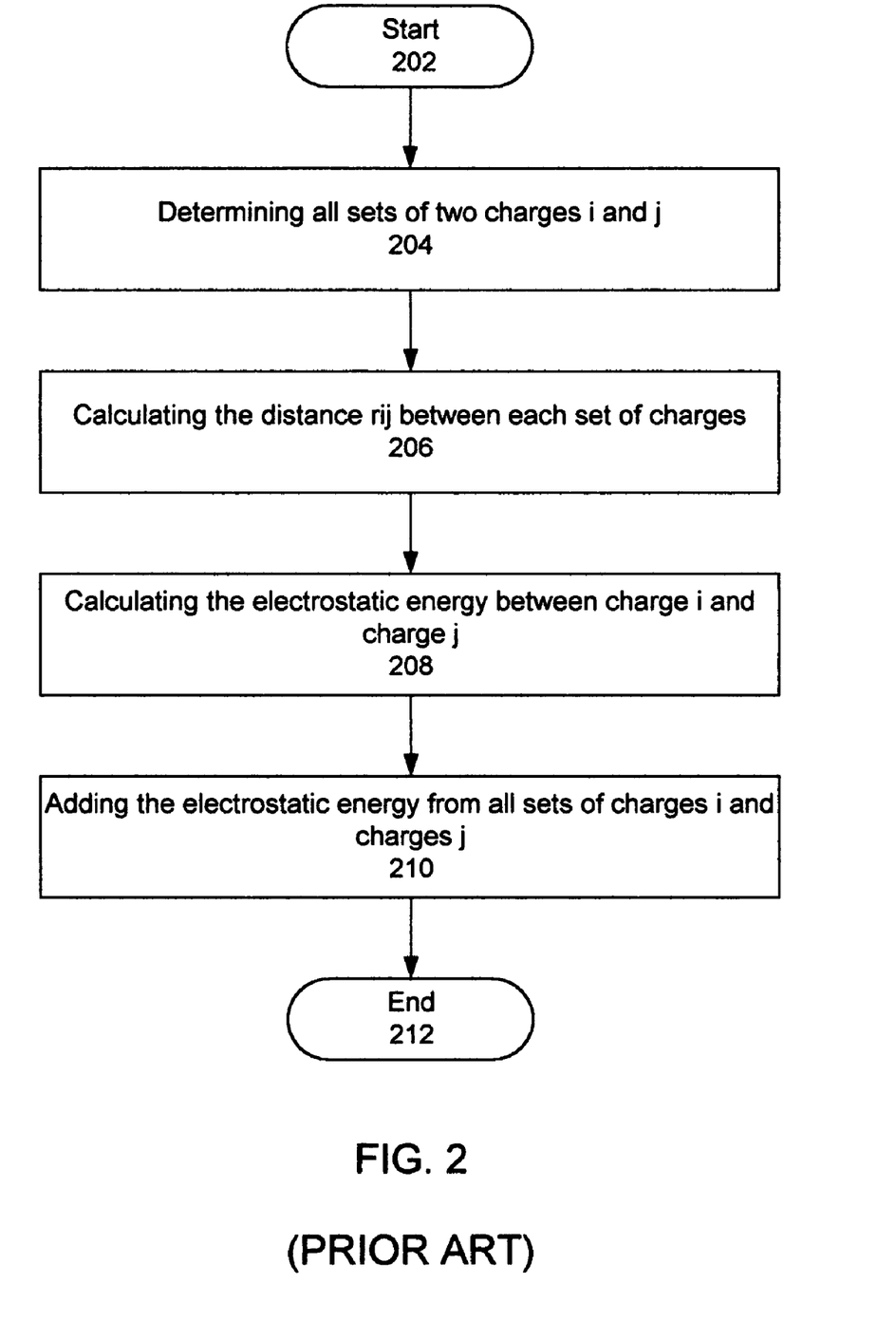
FIG. 2 illustrates a flowchart of a prior art method to calculate electrostatic energy.

FIG. 2 illustrates a flowchart of a prior art method to calculated electrostatic energy. The method starts in operation 202. Operation 204 is next and includes determining all sets of two charges i and j. Operation 206 is next and includes calculating the distance $r_{ij}$ between each set of charges i and j. Operation 208 is next and includes calculating the electrostatic energy between charge i and charge j. Operation 210 is next and includes adding the electrostatic energies from all sets of charges i and j. The method ends in operation 212.

As can be seen from the preceding discussion, the prior art methods for approximating potential energy functions are frequently not practical for complex molecular modeling involving many atoms. What is needed is a more accurate approximation of potential energy functions for molecular modeling, which will provide sufficient accuracy for the modeling of even complex groups of atoms.

SUMMARY OF THE INVENTION

The present invention provides a method and system for molecular modeling. Embodiments of the invention can be implemented in numerous ways, such as a method, a programmable logic device, or a program stored on electronically-readable media. Four aspects of the invention are described below.

A first aspect of the invention is directed to a method to molecularly model a chemical system. The method includes determining a plurality of charges at a plurality of charge positions in a molecular system to be modeled; providing a dielectric function that reflects a plurality of dielectric functions found in a plurality of models, wherein for at least one electrostatic/electrodynamics calculation between two or more charges (or charge distributions) having a separation distance, the separation distance is divided into regions where a plurality of different models apply; and calculating electrostatic energy between the two charges (or charge distributions).

A second aspect of the invention is again directed to a method to model the potential energy function that models a chemical system, where the invention is used for at least one calculation of the electrostatic/electrodynamics energy between two charges or charge distributions. The method includes establishing a first portion of the electrostatics/electrodynamics equation where a charge model uses a dielectric function and assigning the dielectric function to the first portion; assigning a chemically appropriate dielectric function for a second portion; and modeling an electrodynamics equation that provides acceptable accuracy for a neighborhood of the atoms associated with the first portion, wherein the modeling accommodates a switch from a first dielectric of the first portion to a second dielectric of the second portion.

A third aspect of the invention is directed to a program embodied on electronically-readable media, containing instructions to model at least one portion of a molecular system. The program includes a program code segment that establishes a first portion of the electrostatics/electrodynamics equation where a charge model assigns a dielectric function to the first portion; a program code segment to assign a chemically appropriate dielectric function for a second portion of the electrostatics/electrodynamics equation; and a program code segment to model an electrodynamics equation that provides acceptable accuracy for a neighborhood of the atoms used to develop the charge model, wherein the modeling accommodates a switch from a first dielectric of the first portion to a second dielectric of the second portion of the electrodynamics/electrostatics equation.

A fourth aspect of the invention is again directed to a method to model the potential energy function that models a chemical system, where groups of charges are chosen that have a combined charge that is substantially smaller than the individual charges and the combined charge is used, instead of the individual charges, as dictated by the details of the calculation and computer, programmer, and user resources.

DETAILED DESCRIPTION OF THE PREFERRED EMBODIMENT

A model is provided to incorporate different assumptions regarding the dielectric capacity of materials for use in molecular modeling calculations. The charge distribution in molecules is frequently modeled as a function of point charges, dipoles and/or higher multipoles. For a test charge in the periphery of the molecule, the electrostatic potential is calculated with the Poisson Equation using the charge model dielectric. When the test charge is a distance from the molecule, there may be dielectric material between the molecule and the test charge and the electrostatic potential is modified by the presence of this dielectric. The invention accommodates the need for a dielectric term that changes according to the circumstances. The dielectric function is implemented in software on a data processing system (e.g., a general-purpose computer, a personal computer, a hand-held device, or an equivalent).

The electrostatic field outside a group of charges can be modeled as a function of the net charge combined with a dipole term and higher order terms. The choice of which charges to group together effects the stability of the approximation. In embodiments reviewed below several groupings of charges are provided which take advantage of features of chemistry and charge models to increase function stability and to reduce computer time required. The resulting approximation in one embodiment is implemented in software on a data processing system.

Dielectric Function

One embodiment of the invention provides a means to model a dielectric function that takes into account the assumptions made during the development of the charge model, the 'screening' effect that atoms have on electrostatic potential on a molecular scale, and the macroscopic concept of a dielectric. For example, in the charge model of Kollman et al., the charges reproduce the calculated electrostatic field about the molecule for a dielectric of one. When there are two molecules, Coulomb's equation describes the interaction energy between them, again with a dielectric of one. When there is a third molecule between the two molecules, the third molecule has dielectric properties larger than one and the dielectric effect of the third molecule should be incorporated into the equation for the electrostatic potential. A model is needed that incorporates the dielectric effect of the third molecule while maintaining the equation used for two molecules with vacuum between.

Figure 3A:
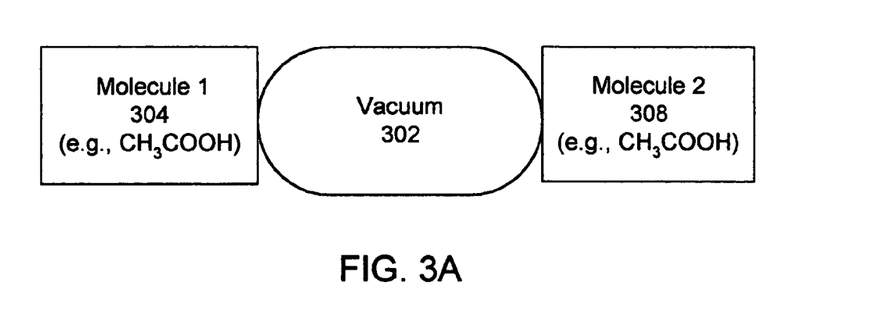
FIG. 3A illustrates two molecules separated by vacuum.

FIG. 3A illustrates a molecule 304 (e.g., $CH_3COOH$) and a molecule 308 (e.g., $CH_3COOH$) separated by vacuum 302.

Figure 3B:
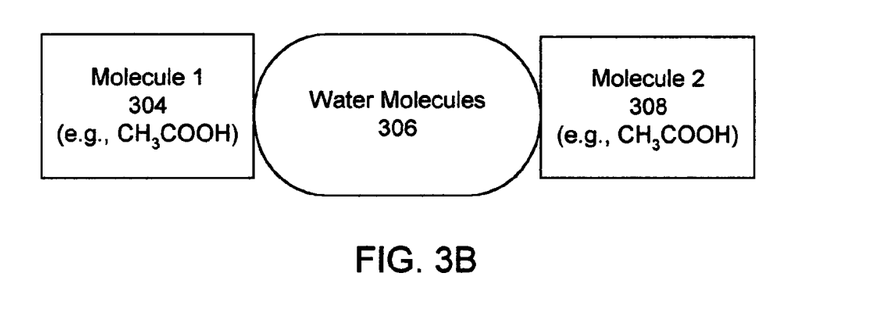
FIG. 3B illustrates two molecules separated by one or more water molecules.

FIG. 3B illustrates a molecule 304 (e.g., $CH_3COOH$) and a molecule 308 (e.g., $CH_3COOH$) separated by one or more water molecules 306.

Figure 3C:
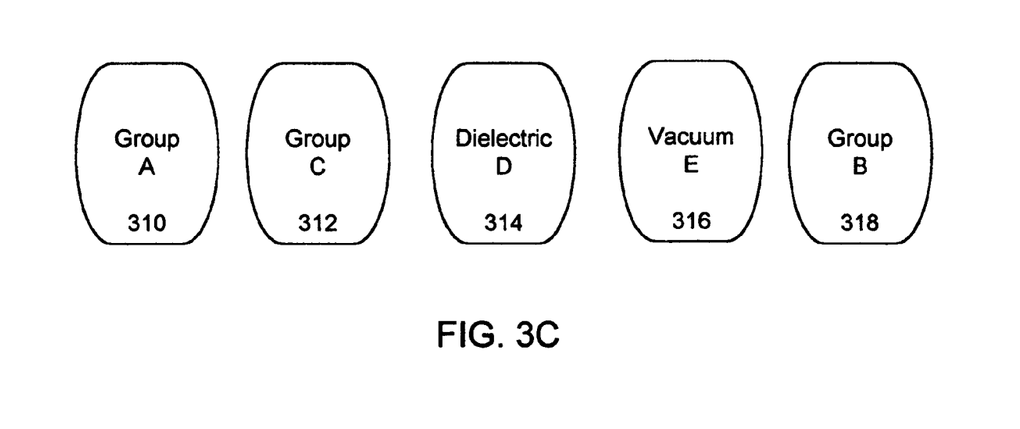
FIG. 3C illustrates a first group of atoms and a second group of atoms, which are in a spatial relationship with one another.

FIG. 3C is an illustration of a first group A of atoms 310 and a second group B of atoms 318, which are in spatial relationship with one another. There may be a third group C of atoms 312, generalized dielectric D 314, or vacuum E 316 between groups A of atoms 310 and group B of atoms 318. In some applications, the first group A of atoms 310 may comprise all of or a portion of a first molecule, and the second group B of atoms 318 may comprise all or a portion of a second molecule. Alternatively, the first group A of atoms 310 and the second group B of atoms 318 may comprise different portions of the same molecule. The first group A of atoms 310 and the second group B of atoms 318 are frequently substructures for which a charge model has been developed.

The electrostatic calculation for charges within a group are determined by the details of charge model development. Electrostatic calculation involving charges in different group A of atoms 310 and group B of atoms 318 with no third group C of atoms 312, or dielectric D 314, between them is calculated using the standard equation for the chosen charge model and/or application.

Figure 4A:
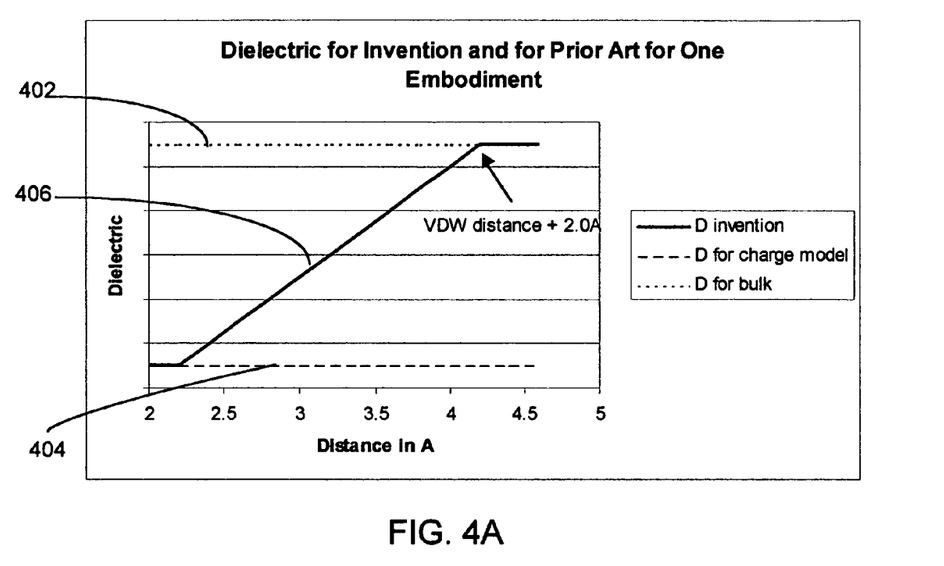
FIG. 4A illustrates a comparison of dielectric value calculated by a prior art method and by one embodiment of the invention.

For the case where there are molecules, a third group C of atoms 312, and/or dielectric D 314, between charges, there are several options. The first option is to use a standard macroscopic equation for vacuum and for the volume of the molecules/dielectric. The second option is to use a vacuum equation for the nearest neighbor atoms and dielectric for atoms further away for a chosen definition for nearest neighbor atoms. The third option is to model the dielectric with a function that is one for distances smaller than the van der Waals distance or other specific distance, where the function varies linearly from 1 at van der Waals distance to a desired bulk dielectric at a distance determined to give sufficient accuracy (for example, the van der Waals distance plus 2.0 Angstroms), and is the bulk dielectric value at distances greater than the specified distance as depicted in FIG. 4A. The fourth option for modeling a dielectric material, for example $H_2O$, is to separate the dielectric capacity from dielectric effects due to different factors such as orientation and polarization, and handle the calculations accordingly. The fifth option is to model the dielectric with a function that assigns a dielectric capacity for each atom type, and assume the dielectric is spherically distributed about the nuclei. The sixth option is to use any other model that incorporates the dielectric impact of atoms, molecules, ions, or any other matter. The seventh option is a model development that uses an explicit variable or a constant dielectric when developing the charge model. This model would use any of the above methods to handle dielectric impact outside the group of atoms. The eighth option is a model development where the dielectric function is incorporated into a charge model that takes into consideration both the electrostatic interaction within the group, and between group A of atoms 310 and group B of atoms 318.

FIG. 4A illustrates a comparison of dielectric value calculated by a prior art method and by one embodiment of the invention. The dotted line 402 shows the bulk C, the dashed line 404 shows the charge model, and the solid line 406 shows the result from one embodiment of the invention.

Figure 4B:
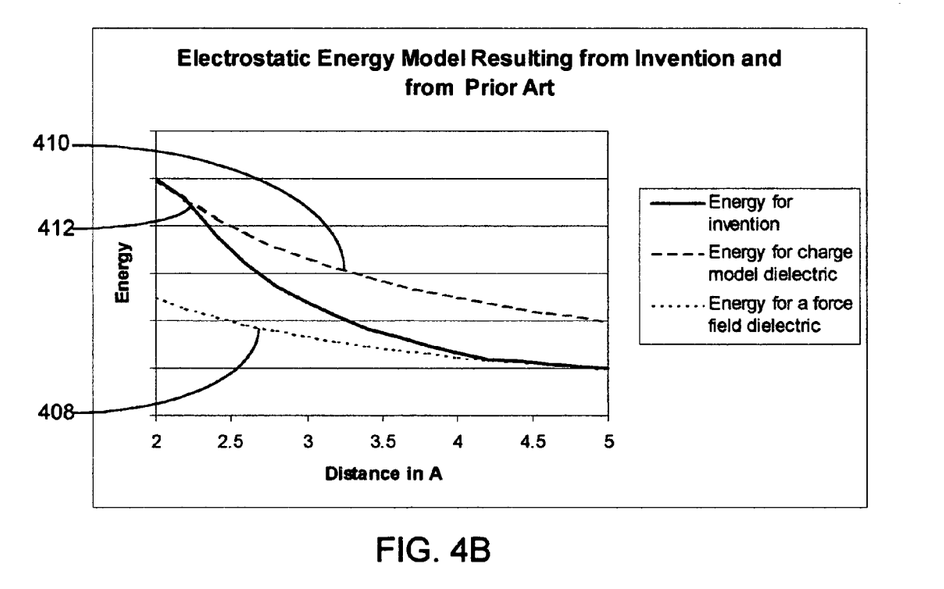
FIG. 4B illustrates a comparison of electrostatic energy calculated by a prior art method and by one embodiment of the invention.

FIG. 4B illustrates a comparison of electrostatic energy calculated by a prior art method and by one embodiment of the invention. The dotted line 408 denotes the energy for a force field dielectric, the dashed line 410 denotes the energy for a charge model dielectric, and the solid line 412 denotes the energy result from one embodiment of the invention.

Composite Charge Model

Several objects and advantages of the composite charge embodiment of invention are to (1) provide an alternate function to estimate electrostatic interaction, (2) reduce the number of electrostatic terms calculated, (3) give electrostatic approximations that are better behaved, and (4) aid the analysis of calculation results. Further objects and advantages of the invention will become apparent from a consideration of the drawings and ensuing description.

Figure 5A:
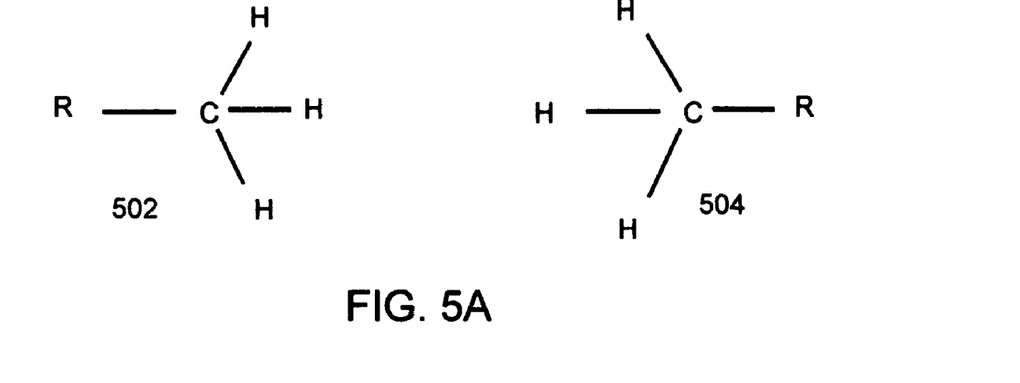
FIG. 5A illustrates two methyl groups to be modeled.

FIG. 5A illustrates two methyl groups 502 and 504 to be modeled.

Figure 5B:
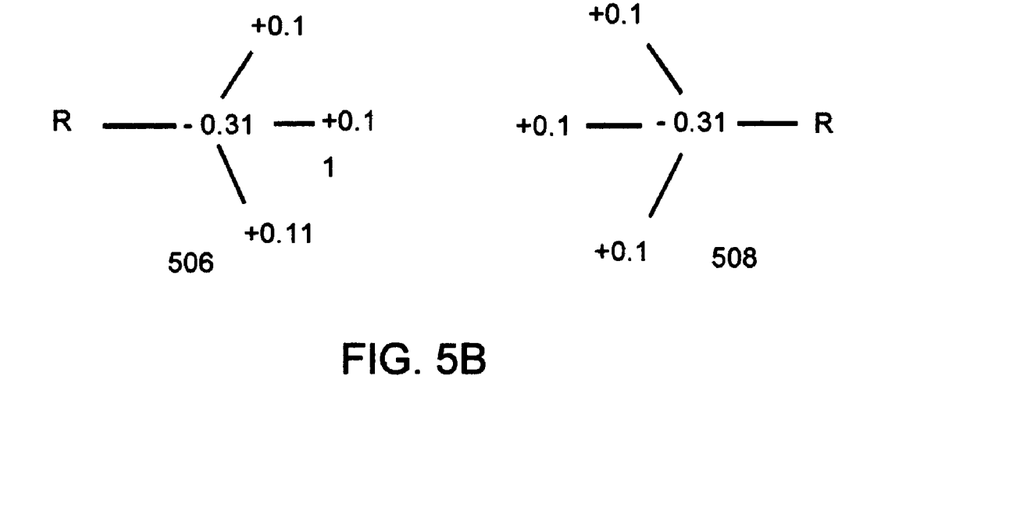
FIG. 5B illustrates two methyl groups modeled by an individual charge model.

FIG. 5B illustrates two methyl groups 506 and 508 modeled by an individual charge model.

Figure 5C:
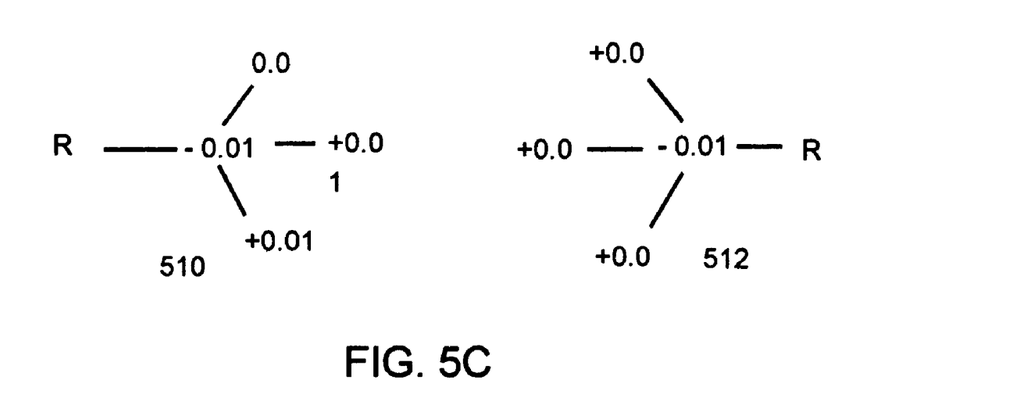
FIG. 5C illustrates two methyl groups modeled by a composite charge model.

FIG. 5C illustrates two methyl groups 510 and 512 modeled by a composite charge model.

Consider the electrostatic potential between a test charge, q, and a methyl group, —CH3, where the test charge is a distance from the methyl group. The electrostatic potential between q and —CH3 using a point charge model for —CH3 is:

$$E = \Sigma_{q>i}(q_q q_i)/(Dr_{qi}) \tag{3}$$

where $q_q$ is the charge of the test charge, $q_i$ are the charges on the —CH3 for a given partial charge model $r_{qi}$ is the distance between charge i and charge q, and D is the dielectric function.

The electrostatic potential approximation is applied, which is described by Lorrain and Corson, as reproduced in the prior art section, where the carbon atom and three attached hydrogens are a set of charges. The charge on each hydrogen is added to the charge of the attached carbon and the point of reference is the position of the carbon nucleus. The dipole and higher multipoles are calculated for the carbon and its attached hydrogens, again the position of the carbon nucleus is the reference point. Then the potential can be modeled as $$E = \Sigma_{q>i}(q_q q_i)/(Dr_{qi}) = k_q \Sigma_{1-3}(q_{total})/(Dr) + k_d \cos\Theta\Sigma_{1-3}(d_{total})/(Dr^2) + k_Q \Sigma_{1-3}(Q_{total})/(Dr^3) \tag{4}$$

where $q_{total}$ is the total charge on —CH3, $d_{total}$ is the total dipole on —CH3, $Q_{total}$ is the total quadrupole on —CH3, $K_q$, $k_d$, and $k_Q$ are conversion constants; $r_{qi} > r_{methyl}$; $r_{methyl}$ = the largest dimension of the methyl group.

The total charge on the methyl group is near zero and $q_{total} \sim 0$. The interaction between a point charge and a multipole is small since the terms drop off rapidly with distance, and the second and higher order terms are also small. The first term in equation (4) is the only significant term and the error in the composite charge model is linear in 1/r. The determination of the distance needed for the desired accuracy depends on the dielectric constant (D) of the material between the two charges and the demands of the calculation.

In this example, the invention uses one term. Compare this with the approximation formerly used in equation (3), which contains 4 terms. This substantial savings is common due to the character of computer generated charge models. The charge models generally use oppositely signed charges in close proximity to each other to model quantum mechanics effects. The charges are classical mimics of quantum results in the immediate vicinity of a molecule. The fields from these opposing charges rapidly drop off and can be approximated by the sum of the charges at moderate distances, where a moderate distance is the second or third sphere of nearest neighbors. As a result, the first term in equation (4) tends to be small and is frequently zero. In either case it can be set to zero for sufficiently large r. The remaining terms, the dipole term and higher multipole terms, tend to decrease rapidly with distance and can frequently be set to zero. However, the multipole terms occasionally play an important role in aggregate and need to be considered carefully. For example, molecules are expected to orient about an ion and the aggregate dipole becomes significant. The aggregate multipole terms could be sampled every n iterations and then handled as appropriate. However, in general, the net electrostatic potential at a distance from a molecule tends to be small as compared to the electrostatic potential due to the partial charge on a single atom.

In one embodiment of the invention, atoms are grouped by molecule, side-chain, or other division. For every group, a reference position point (x, y, z) is chosen that is within the region of the group and the charges associated with the atoms are analyzed to produce total charge, dipole and higher multipoles centered on the reference point. Frequently dipole and/or higher multipoles can be ignored. This description of the charge distribution is then used for the electrostatic calculation for all points greater than r Angstroms away from the reference point, where r is chosen based on the dielectric and the desired accuracy. In this approximation, r must be greater than the greatest distance between the reference point and all atoms. Examples of groups are $H_2O$, the backbone atoms in an amino acid, side-chains of amino acids, an ion and its counter ion, all neutral molecules, and all atoms in a molecule except for a subgroup (e.g., in nitropentane, all atoms except $-NO_2$).

In one preferred embodiment, every heavy atom and all the attached hydrogen atoms are considered to be a group; the charges on hydrogen atoms are added to the charge on the attached heavy atom. A convenient reference point is the heavy atom center. In an electrostatic calculation, the complete equation (3) is used when the heavy atom is less than r Angstroms away. When the distance is greater than r then the individual hydrogen and heavy atom charges are ignored and the summed charge is used. In this embodiment, only the distances to the reference point (e.g., the heavy atoms) need be calculated when the distance is greater than r. In another embodiment, this sum is done for just the carbon heavy atoms, and hetero-atoms are handled using the classical equation (3). Other embodiments include summing all charges in a side chain of an amino acid or other polymer, summing all charges in the monomer backbone, and summing all atoms in a side chain or molecule exclusive of atoms with a formal charge.

In one embodiment, the invention is used to aid analysis of calculations. For example, the charge on hydrogen is added to the charge on the heavy atom it is attached to and the approximation is applied as described above. This step greatly reduces the number of terms calculated, easing the analysis of the remaining terms. In particular if the approximation is applied for all r, this introduces a significant error for small r, but aids analysis of the gross features of the electrostatic field.

One embodiment of the invention is used during the initial stages of a calculation, such as a dynamics calculation, and the complete equation is used at the end and/or intermittently to assure that the end coordinates are a minimum for the complete equation. One embodiment of the invention is used in a quantum mechanics calculation where a group at a sufficient distance away is treated as a point charge, dipole, and multipoles. For example, a water molecule at a distance could be treated as a collection of multipoles. In one embodiment, the invention is used in combination with the invention disclosed by U.S. Pat. No. 5,612,894 or U.S. Pat. No. 5,915,230.

Figure 6:
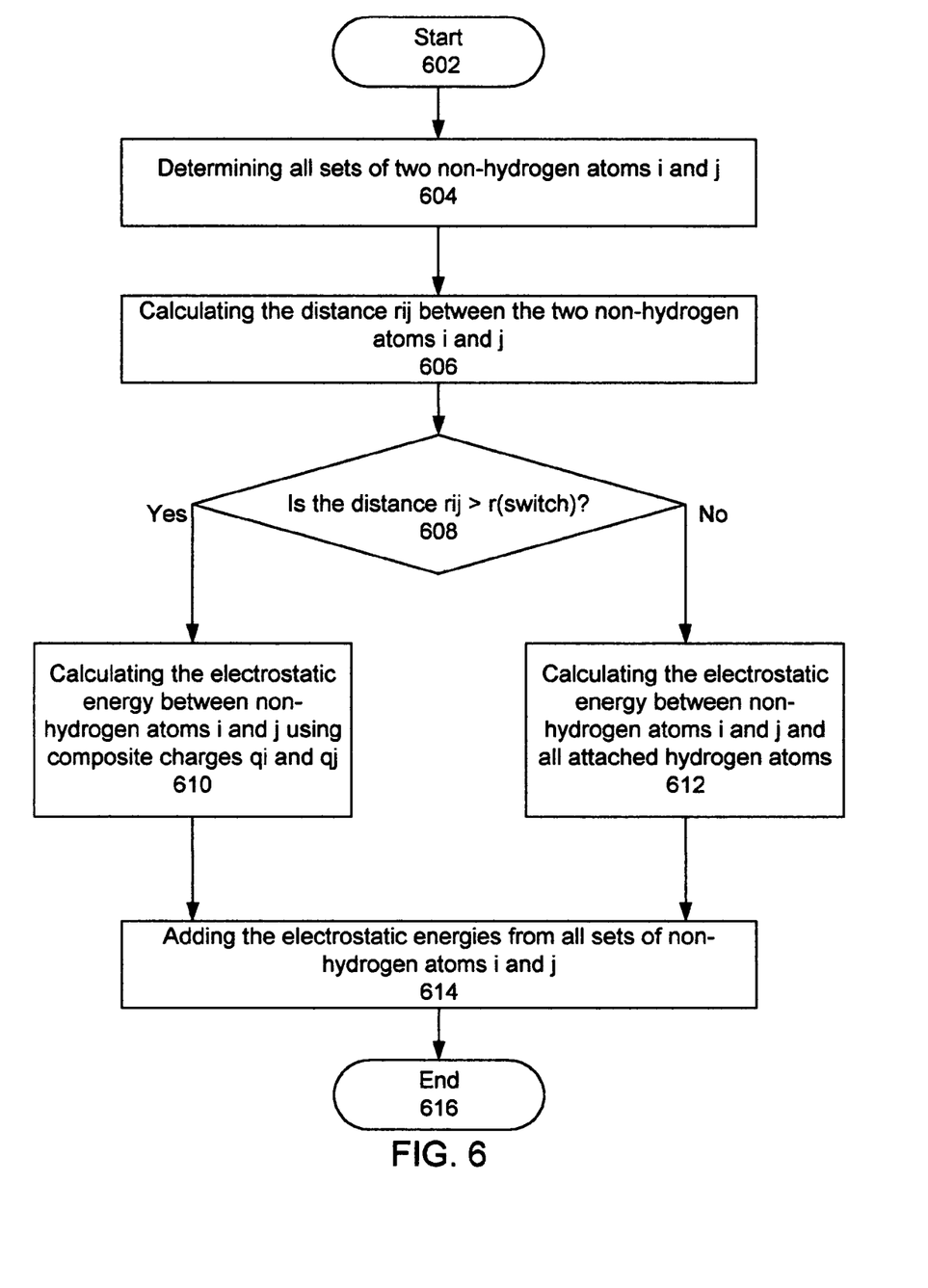
FIG. 6 illustrates a flowchart to model a molecule, in accordance with one embodiment of the invention.

FIG. 6 illustrates a flowchart to model a molecule, in accordance with one embodiment of the invention. The method starts in operation 602. Operation 604 is next and includes determining all sets of two non-hydrogen atoms i and j. Operation 606 is next and includes calculating the distance $r_{ij}$ between the two non-hydrogen atoms i and j. Operation 608 is next where a test is made to determine if the distance $r_{ij}$ is greater than the switching distance r(switch). If the result of the test of operation 608 is yes, then operation 610 is next, which includes calculating the electrostatic energy between non-hydrogen atoms i and j using composite charges qi and qj. If the result of test of operation 608 is no, then operation 612 is next, which includes calculating the electrostatic energy between non-hydrogen atoms i and j and all attached hydrogen atoms. Operation 614 is next and includes adding the electrostatic energies from all sets of the non-hydrogen atoms i and j. The method ends in operation 616.

Figure 7:
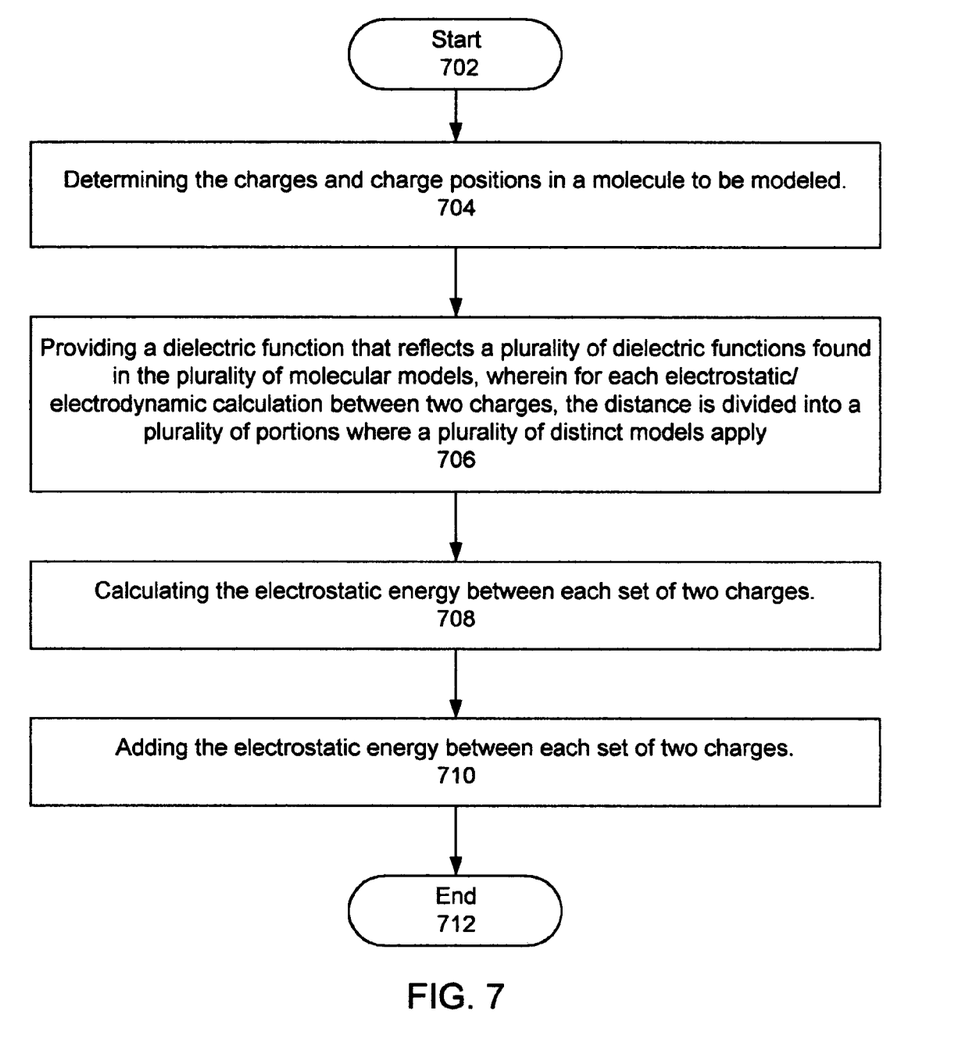
FIG. 7 illustrates a flowchart to model a molecule, in accordance with one embodiment of the invention.

FIG. 7 illustrates a flowchart to model a molecule, in accordance with one embodiment of the invention. The method starts in operation 702. Operation 704 is next and includes determining the charges and charge position in a molecular system to be modeled. Operation 706 is next and includes providing a dielectric function that reflects a plurality of dielectric functions found in a plurality of molecular models, wherein for each electrostatic/electrodynamics calculation between two charges, the distance is divided into a plurality of regions where a plurality of distinct models apply. Operation 708 is next and includes calculating the electrostatic energy between each set of two charges. Operation 710 is next and includes adding the electrostatic energies from each set of two charges. The method ends in operation 712.

Figure 8:
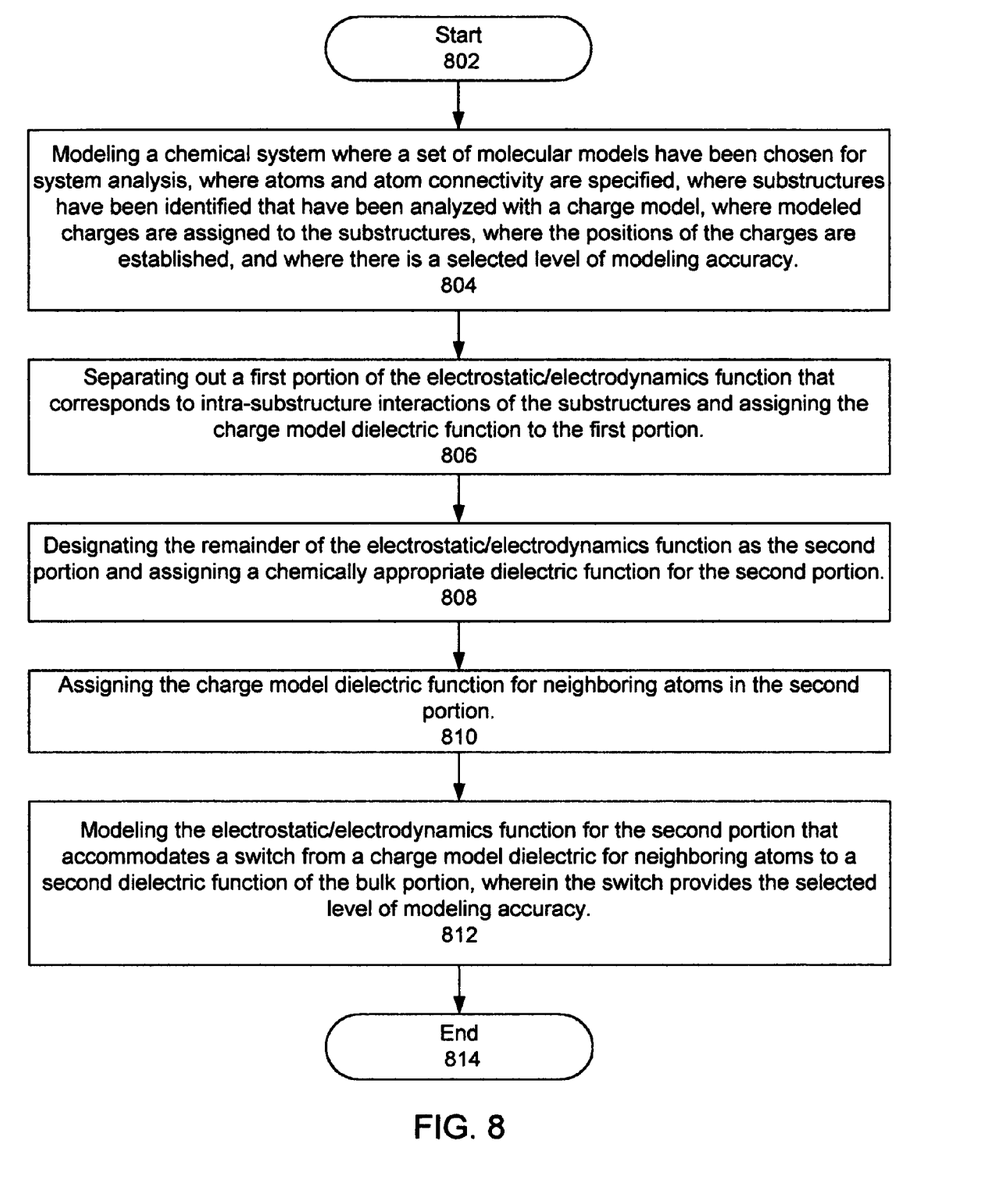
FIG. 8 illustrates a flowchart to model a molecule, in accordance with one embodiment of the invention.

FIG. 8 illustrates a flowchart to model a molecule, in accordance with one embodiment of the invention. The method starts in operation 802. Operation 804 is next and includes modeling a chemical system where a set of molecular models have been chosen for system analysis, where atoms and atom connectivity are specified, where substructures have been identified that have been analyzed with a charge model, where modeled charges are assigned to the substructures, where the positions of the charges are established, and where there is a selected level of modeling accuracy. Operation 806 is next and includes separating out a first portion of the electrostatic/electrodynamics function that corresponds to intra-substructure interactions of the substructures and assigning the charge model dielectric function to the first portion. Operation 808 is next and includes designating the remainder of the electrostatic/electrodynamics function as the second portion and assigning a chemically appropriate dielectric function for the second portion. Operation 810 is next and includes assigning the charge model dielectric function for neighboring atoms in the second portion. Operation 812 is next and includes modeling the electrostatic/electrodynamics function for the second portion that accommodates a switch from a charge model dielectric for neighboring atoms to a second dielectric function of the bulk portion, wherein the switch provides the selected level of modeling accuracy. The method ends in operation 814.

Figure 9:
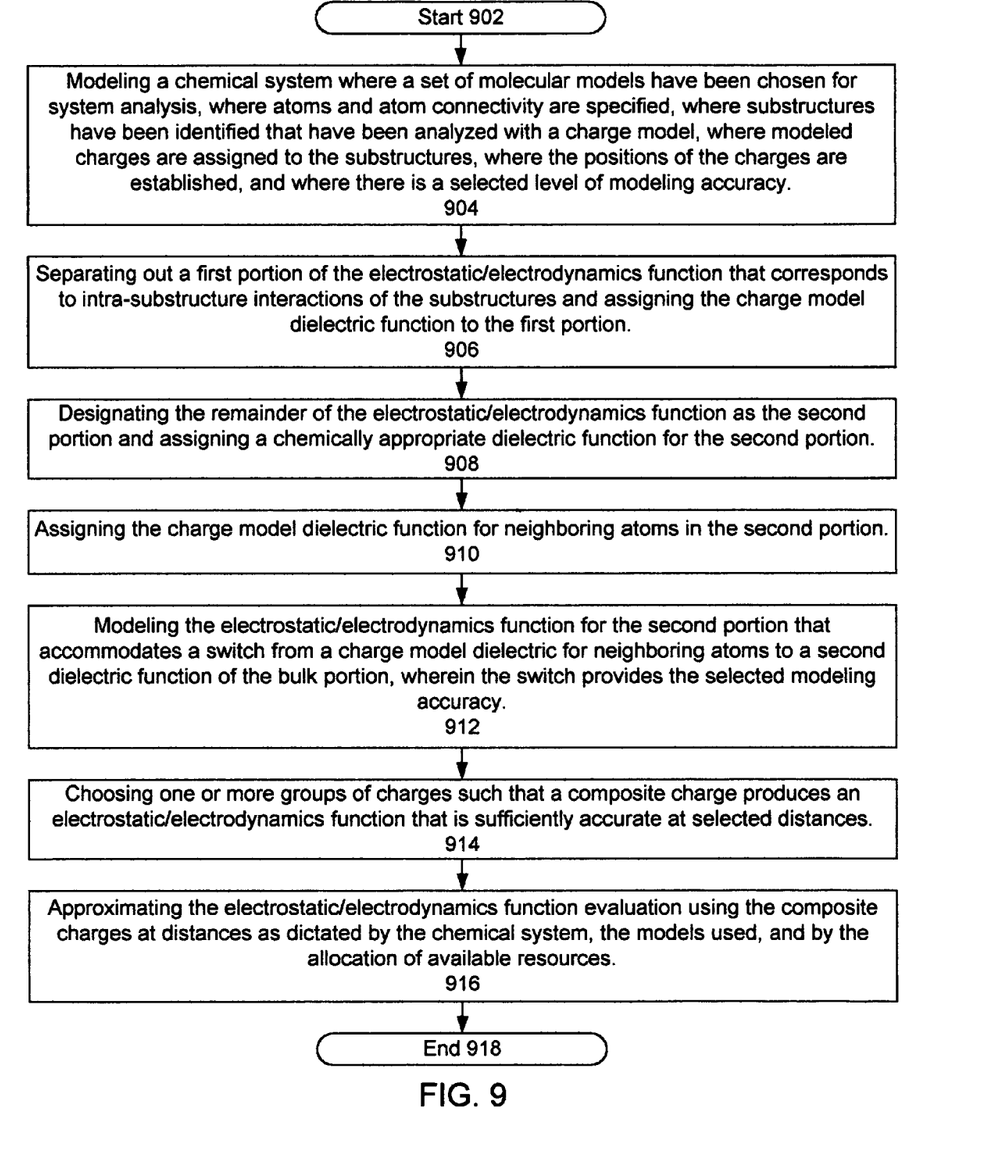
FIG. 9 illustrates a flowchart to model a molecule, in accordance with one embodiment of the invention.

FIG. 9 illustrates a flowchart to model a molecule, in accordance with one embodiment of the invention. The method starts in operation 902. Operation 904 is next and includes modeling a chemical system where a set of molecular models have been chosen for system analysis, where atoms and atom connectivity are specified, where substructures have been identified that have been analyzed with a charge model, where modeled charges are assigned to the substructures, where the positions of the charges are established, and where there is a selected level of modeling accuracy. Operation 906 is next and includes separating out a first portion of the electrostatic/electrodynamics function that corresponds to intra-substructure interactions of the substructures and assigning the charge model dielectric function to the first portion. Operation 908 is next and includes designating the remainder of the electrostatic/electrodynamics function as the second portion and assigning a chemically appropriate dielectric function for the second portion. Operation 910 is next and includes assigning the charge model dielectric function for neighboring atoms in the second portion. Operation 912 is next and includes modeling the electrostatic/electrodynamics function for the second portion that accommodates a switch from a charge model dielectric for neighboring atoms to a second dielectric function of the bulk portion, wherein the switch provides the desired modeling accuracy. Operation 914 is next and includes choosing one or more groups of charges such that a composite charge produces an electrostatic/electrodynamics function that is sufficiently accurate at selected distances. Operation 916 is next and includes approximating the electrostatic/electrodynamics function evaluation using the composite charges at distances as dictated by the chemical system, the models used, and by the allocation of available resources (e.g., computer, programmer, and user resources). The method ends in operation 918.

Figure 10:
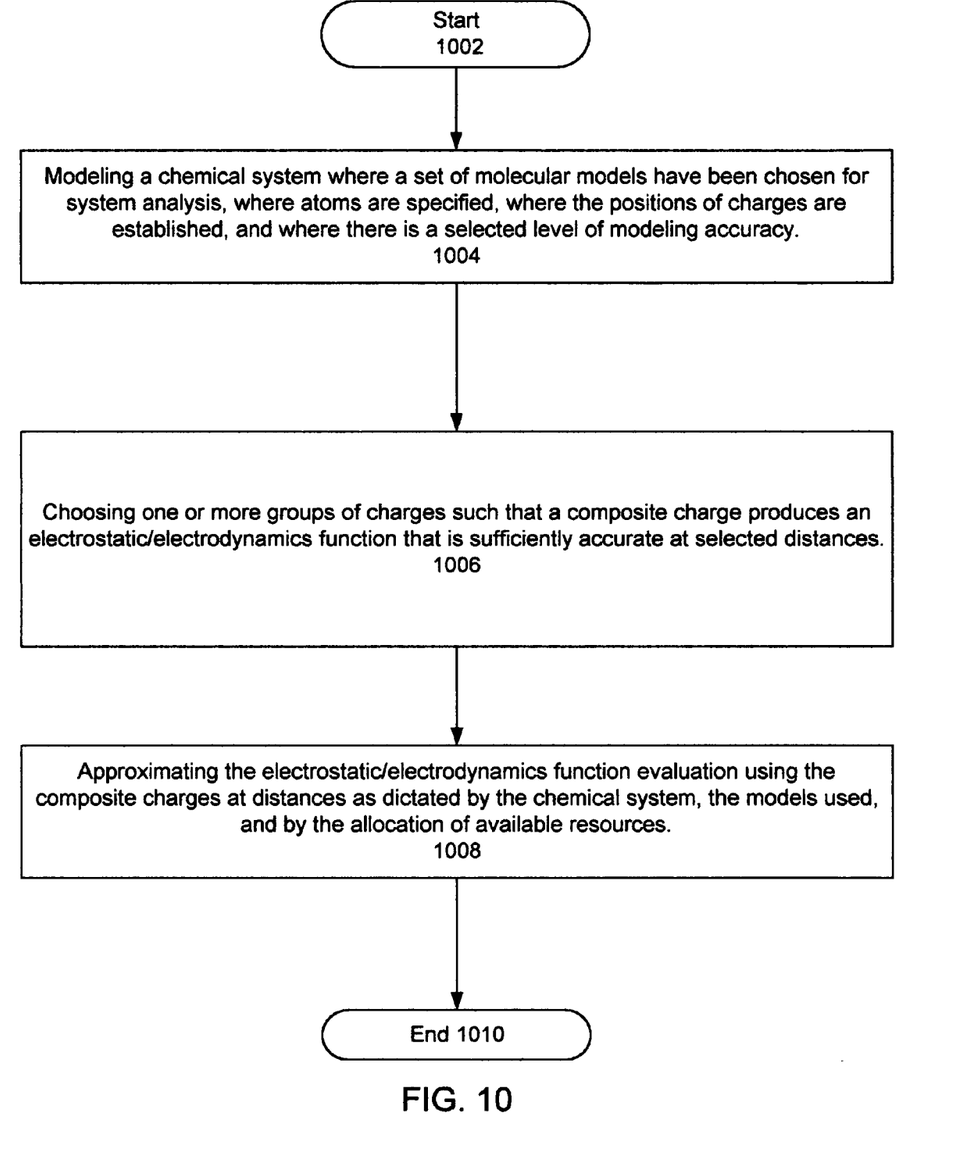
FIG. 10 illustrates a flowchart to model a molecule, in accordance with one embodiment of the invention.

FIG. 10 illustrates a flowchart to model a molecule, in accordance with one embodiment of the invention. The method starts in operation 1002. Operation 1004 is next and includes modeling a chemical system where a set of molecular models have been chosen for system analysis, where atoms are specified, where the positions of the charges are established, and where there is a selected level of modeling accuracy. Operation 1006 is next and includes choosing one or more groups of charges such that a composite charge produces an electrostatic/electrodynamics function that is sufficiently accurate at selected distances. Operation 1008 is next and includes approximating the electrostatic/electrodynamics function evaluation using the composite charges at distances as dictated by the chemical system, the models used, and by the allocation of available resources (e.g., computer, programmer, and user resources). The method ends in operation 1010.

Figure 11:
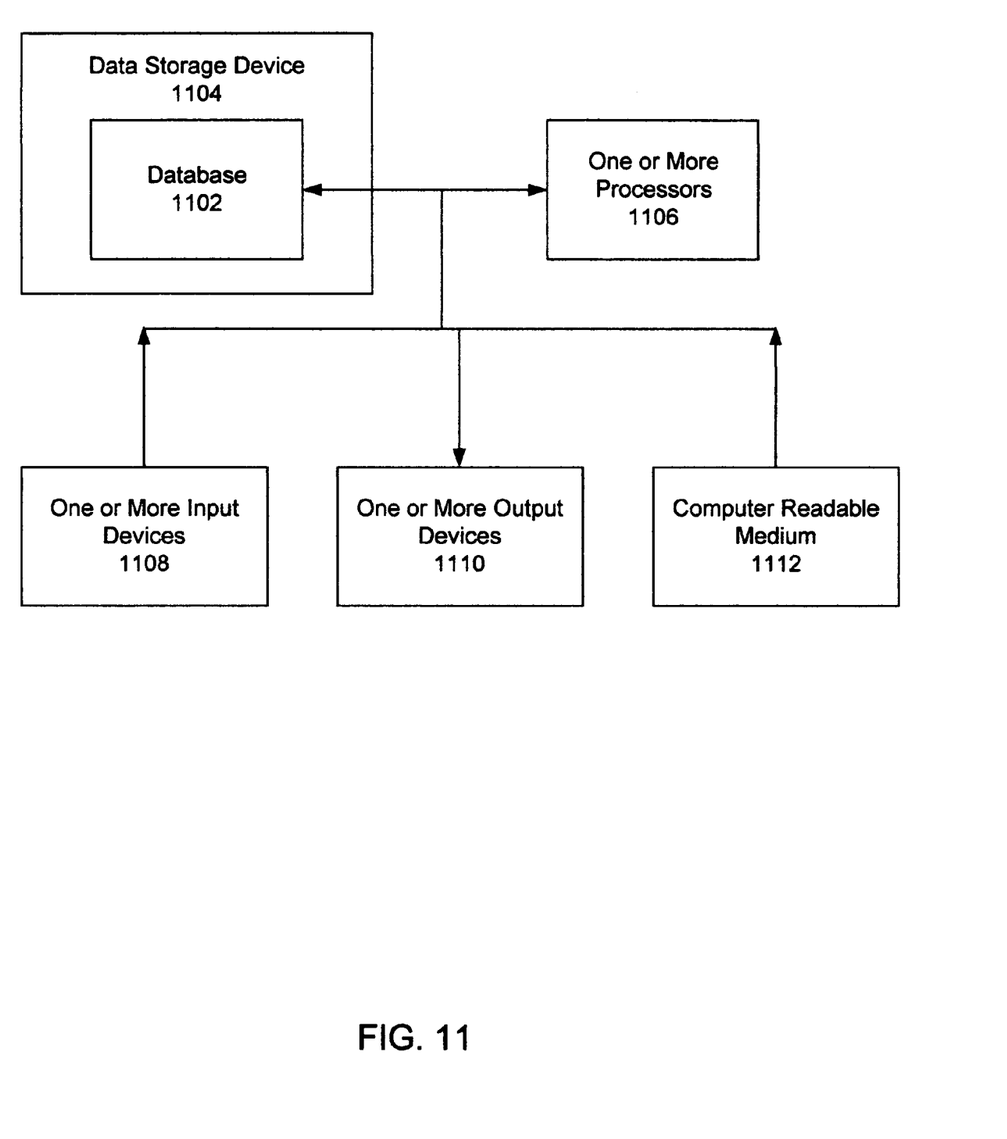
FIG. 11 illustrates a block diagram of a data processing system to model molecules, in accordance with one embodiment of the invention.

FIG. 11 illustrates a block diagram of a data processing system to model molecules, in accordance with one embodiment of the invention. The data processing system has access to a database 1102 of charges, atomic positions, interaction parameters and/or any other necessary data; which is stored in a data storage device 1104, such as a CD-ROM, magnetic disk, semiconductor integrated circuit memory or an equivalent memory device. One or more processors 1106 access the database 1102 and perform the electrostatic calculations. One or more input devices 1108 and output devices 1110 provide a user interface, such as keyboards, graphical user interface, printer, and equivalents. Commands to configure this data processing system to implement one embodiment of the invention, are stored on a computer readable medium 1112, such as a CD-ROM or an equivalent, for access by the data processing system.

Other embodiments of the invention are possible. For example, the invention may be used in quantum mechanical (QM)/molecular modeling (MM) calculations. The model for the dielectric that accommodates the switch from a charge model dielectric to bulk dielectric may be used for calculations across the QM-MM border. The composite charge methods could be used in a generalization of QM/MM methods where all interactions at a large distance are handled with MM. The invention may be used in conjunction with other models, such as generalized Born calculations, Poisson-Boltzmann calculations, and other condensed phase methods. The invention may also be used with other charge models such as a charge model based on Artificial Intelligence techniques (e.g. a knowledge based system), a charge model based on the wavefunction developed in a quantum mechanics equation using Mulliken charges, or on a model derived from Mulliken charges.

The exemplary embodiments described herein are for purposes of illustration and are not intended to be limiting. Therefore, those skilled in the art will recognize that other embodiments could be practiced without departing from the scope and spirit of the claims set forth below.

What is claimed is:

1. A method to molecularly model electrostatic interactions in a homogeneous portion of a chemical system with a plurality of charges from a charge model, each said charge at a defined position, said method comprising:
providing a dielectric function that is selected from a plurality of dielectric functions found in a plurality of models; and
calculating, by use of a data processing system specifically programmed with software to implement said dielectric function, an electrostatic energy between a plurality of sets of two charges in said chemical system to reduce a development time required to develop at least one new material with one or more desirable properties, wherein a plurality of distinct models apply.

2. The method of claim 1, wherein a plurality of distinct combinations of molecular models are applied to model said dielectric function.

3. The method of claim 1, wherein said charges are replaced by one or more composite charges or one or more composite charge distributions.

4. The method of claim 1, wherein said chemical system includes a selected combination of chemical substructures chosen from a list of chemical substructures consisting of a molecule, ion, amino acid, nucleic acid, monomer, polymer, or any group of one or more atoms, where an electrostatic characteristics of said selected combination of chemical substructures is modeled with a charge model.

5. The method of claim 4, wherein a region, of a plurality of regions where a plurality of distinct molecular models apply, is spanning the space between or near a chemical substructure and one or more nearest neighbor substructures of said chemical substructure.

6. The method of claim 5, wherein the dielectric function is 1 for said distances that are nearest neighbor distances and where, for at least 20% of the said separation distances sufficiently large for classical electrostatic equations to apply, said dielectric function has a value that is within 70% to 150% of 4 for said homogeneous portion.

7. The method of claim 4, wherein a region, of a plurality of regions where a plurality of distinct molecular models apply, is within or near a van der Waals distance for all said chemical substructures.

8. The method of claim 7, wherein for said region where classical electrostatic equations apply, said provided dielectric function has a value that is within 70% to 150% of 4 for said homogeneous portion.

9. The method of claim 4, wherein a region, of a plurality of regions where a plurality of distinct molecular models apply, includes a distance within one of said selected substructures.

10. The method of claim 9, wherein for said region where classical electrostatic equations apply, said provided dielectric function has a value that is within 70% to 150% of 4 for said homogeneous portion.

11. The method of claim 10, wherein said chemical system has a homogeneous protein portion and a homogeneous aqueous portion.

12. The method of claim 1, wherein a polarization can be described with a dielectric function with a component linear with an electrostatic field, and wherein said dielectric function models an effect of said polarization.

13. The method of claim 1, wherein one said dielectric function of a plurality of dielectric functions models an effect due to an electronic polarization.

14. The method of claim 13, wherein one or more electrostatic calculations use one or more analytical classical equations.

15. The method of claim 1, wherein there is at least one nearest-neighbor separation distance and at least one said nearest-neighbor separation distance is sufficiently large for one or more bulk electrostatic equations to apply.

16. The method of claim 15, wherein a force field model uses said dielectric function during a force field model development.

* * * * *